(12) United States Patent
Jin et al.

(10) Patent No.: US 7,884,129 B2
(45) Date of Patent: Feb. 8, 2011

(54) COMPOSITION COMPRISING THE ALCOHOL COMPOUND ISOLATED FROM THE EXTRACT OF CUCURBITACEAE FAMILY PLANT HAVING ANTI-ADIPOGENIC AND ANTI-OBESITY ACTIVITY

(75) Inventors: Mi Rim Jin, Seoul (KR); Jae Ha Ryu, Seoul (KR); Hyoun Jeong Choi, Incheon (KR); Hyun Jin Jung, Seoul (KR); Kyoung Chul Park, Seoul (KR); Sun Young Kim, Seoul (KR)

(73) Assignee: Helixir Co., Ltd., Seoul (KR)

( * ) Notice: Subject to any disclaimer, the term of this patent is extended or adjusted under 35 U.S.C. 154(b) by 0 days.

(21) Appl. No.: 12/124,131

(22) Filed: May 20, 2008

(65) Prior Publication Data

US 2008/0280976 A1    Nov. 13, 2008

Related U.S. Application Data

(63) Continuation-in-part of application No. 10/581,576, filed as application No. PCT/KR2004/003169 on Dec. 3, 2004, now abandoned.

(30) Foreign Application Priority Data

Dec. 3, 2003    (KR) ............... 10-2003-0087275

(51) Int. Cl.
*A01N 43/08* (2006.01)
*A61K 39/00* (2006.01)

(52) U.S. Cl. .................... 514/469; 514/183
(58) Field of Classification Search .......... 514/469
See application file for complete search history.

(56) References Cited

U.S. PATENT DOCUMENTS 4,421,746 A * 12/1983 Kojima et al. ............... 424/758
2004/0003432 A1 * 1/2004 Obukowicz ................ 800/284

FOREIGN PATENT DOCUMENTS

JP        62209070 A    9/1987

OTHER PUBLICATIONS

Chen et al. (Bitter Melon (*Momordica charantia*) Reduces Adiposity, Lowers Serum Insulin and Normalizes Glucose Tolerance in Rats Fed a High Fat Diet, The American Society for Nutritional Sciences J. Nutr. 133: 1088-1093, Apr. 2003, printed pp. 1-13.*
Acosta-Patino, JL et al., Hypoglycemic action of *Cucurbita ficifolia* on Type 2 diabetic patients with moderately high blood glucose levels, J. Ethnopharma., 77 (2001), 99-101.
Noguchi, R. et al., Dietary effects of Bitter Gourd Oil on Blood and Liver Lipids of Rats, Arch. Biochem. Biophysics, 396, 2, 207-212, 2001.
Senanayake, Gvk et al., The effects bitter melon (*Momordica charantia*) on serum and lover triglyceride levels in rats, J. Ethnopharma, 91 (2004), 257-262.
Sathishekar, D et al., Beneficial Effects of *Momordica charantia* seeds in the treatment of STZ-Induced Diabetes in Experimental Rats, Biol. Pharm Bull, 38(6) 978-983, 2005.
Chaturuvedi, P. et al., Effect of *Momordica charantia* on Lipid Profile and Oral Glucose Tolerance in Diabetic Rats, Phytotherapy Res., 18, 954-956, 2004.
Quanhong, L. et al., Effects of protein-bound polysaccharide isolated from pumpkin on insulin in diabetic rats, Plant Foods Human Nutr., 60, 13-16, 2005.
Xia, T, et al., Antohyperglycemic effect of *Cucurbita ficifolia* fruit extract in streptozocin-induced diabetic rats, Fitoterapia, 77, 530-533, 2006.
Chan, Lly et al., Reduced adiposity in bitter melon (*Momordica charantia*)-fed rats is asscoiated with increased lipid oxidative enzyme activities and uncoupling protein expression, J. Nutr., 2005 135: 2517-2523.
Juhasz et al, "A new approach for the synthesis of naturally occurring dihydrobenzo[b]furan-type neolignans of potential biological activity", Tetrahedron Letters 2000 41, 2491-2494.
Zidek et al., "Intracellular electrolytes and hormonal parameters during weight reduction" Ann. Nutr. Metab, 1984, 28(2), 65-69.
Okazaki et al., Steroselective synthesis of the neolignan, (+)-dehydrodiconiferyl alcohol, Biosci Biotechnol. Biochem 2001, 65(5), 1134-1140.
Ailhaud, "Molecular mechanism of adipocyte differentiation", J. Endocrinol. 1997, 155, 201-202.

* cited by examiner

*Primary Examiner*—Sreeni Padmanabhan
*Assistant Examiner*—Timothy E Betton
(74) *Attorney, Agent, or Firm*—Hogan Lovells US LLP (57) ABSTRACT

The present invention is related to an alcohol compound isolated from the extract of Cucurbitaceae family plant having anti-adipogenic and anti-obesity activity, and a composition comprising the same. The compound showed potent reducing activity of body weight, decreasing effect on the blood triglyceride and cholesterol level, activating activity of PPAR α and preventing activity from the adipogenesis of precursor fat cells with no toxicity, therefore, those extract can be useful in treating or preventing obesity and adipogenesis-involved diseases as a medicine or health care food.

5 Claims, 3 Drawing Sheets

COMPOSITION COMPRISING THE ALCOHOL COMPOUND ISOLATED FROM THE EXTRACT OF CUCURBITACEAE FAMILY PLANT HAVING ANTI-ADIPOGENIC AND ANTI-OBESITY ACTIVITY

This application is a Continuation-in-Part of U.S. Non-provisional application Ser. No. 10/581,576 filed on May 17, 2007 (pending), which claims priority upon International Application PCT/KR2004/3169, filed on Dec. 3, 2004, which claims priority to Korean Patent Application No. 10-2003-0087275, filed on Dec. 3, 2003. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a composition comprising the alcohol compound isolated from the extract of Cucurbitaceae family plant having anti-adipogenic and anti-obesity activity.

BACKGROUND ART

Adipogenesis is a process to differentiate preadipocytes into mature adipocytes and accumulate lipids in cytoplasmic organelles named of lipid droplets, which is known to be a risky factor which may give rise to various adult diseases such as obesity, diabetes, steatosis and coronary heart disease. Precursor fat cells such as fibroblasts can be differentiated into mature ones resulting in the formation of lipid droplets within them. The differentiation mechanism has been studied by using specific cell lines such as 3T3-L1. Adipocyte differentiation is a complex process accompanied by coordinated changes in morphology, hormone sensitivity, and gene expression. These changes are regulated by several transcription factors such as C/EBPs (CAAT enhancer binding proteins), PPARs (Peroxisome Proliferator-Activated receptors), and ADD/SREBPs (Adipocyte determination and differentiation dependent factor 1/sterol regulatory element-binding proteins). (Bart A Jessen et al., *Gene*, 299, pp 95-100, 2002; Darington et al., *J. Biol. Chem.*, 273, pp 30057-30060, 1998; Brun R. P et al., *Curr. Opin. Cell. Biol.*, 8, pp 826-832, 1996). These transcription factors are induced at different stages of adipocyte differentiation and functionally interact with each other to conduct adipogenesis and lipogenesis by regulating gene expression. For example, C/EBP β and δ factors are temporally overexpressed by the external hormonal stimuli such as MDI (isobutylmethylxanthin, dexamethason and insulin), which triggers adipocyte differentiation process. (Reusch J. E. et al., *Mol. Cell. Biol.*, 20, pp 1008-1020, 2000). Subsequently, they induce the increase of C/EBP α and PPAR γ (James M. N. et al., *J. Nutr.*, 130, pp 3122S-3126S, 2000). Especially, PPAR γ is predominantly expressed in adipocytes and is a key determination transcription factor for adipogenesis, which forms a heterodimer with RXR (Retinoic acid X receptor) and binds to PPRE (Peroxisome Proliferator Response elements) found in promoters of various genes involved in adipogenesis (Tontonoz P. E. et al., *Genes Dev.*, 8, pp 1224-1234, 1994). The interaction between C/EBP α and PPAR γ is crucial in the adipocyte differentiation and those factors control the expression of adipocyte-specific genes such as fatty acid bound protein, aP2 and lipid metabolic enzymes. Especially, ADD1/SREBPs also plays a key role for lipogenesis and insulin-stimulated gene expression, and the expression of ADD 1/SREBP1c contributes to the activation of PPAR γ (Rosen E. D. et al., *Annu. Rev. Cell Dev. Biol.*, 16, pp 145-171, 2000; Osborn T. F., *J. Biol. Chem.*, 275, pp 32379-32382, 2000). The adipocytes finished the differentiation process synthesize lipids and store them in a form of triglycerides.

In the meanwhile, the homeostasis of lipid metabolism is maintained by the balance between synthesis and disintegration of fat. ADD1/SREBP1 controls the synthesis of fatty acid, triglyceride, cholesterol, and phospholipid etc (Horton J. D. et al., *J. Clin. Invest.*, 109, pp 1125-1131, 2002). SREBPs are synthesized as about 1150 amino acid precursors bound to the endoplasmic reticulum and nuclear envelope. To be active, the membrane-bound SREBP must be ptoteloytically cleaved to release the N-terminal segment so that it can enter the nucleus. The cleaved SREBPs, designated the nuclear form, binds to the SRE (sterol regulated elements) in the regulatory gene promoter. The genes regulated by SREBPlc, one of the SREBP isoforms are ACL (ATP citrate lyase), ACC (Acetyl CoA Carboxylase), FAS (Fatty acid synthase), and SCD (Stearoly-CoA desarurase) etc (Osborn T. F. et al., *J. Biol. Chem.*, 275, pp 32379-32382, 2000; Soazig L. L. et al., *J. Biol. Chem.*, 277, pp 35625-35634, 2002). It has been reported that PPAR α plays an important role in regulating lipolysis (Beisiegel U., *Proc. Natl. Acad. Sci. U.S.A.*, 96, pp 13656-13661, 1999) through control of lipid metabolic enzymes such as LPL (lipoprotein lipase), apoproteins, ACO (Acyl-CoA oxidase), thiolase (Dreyer C et al., *Cell*, 68, pp 879-887, 1992).

Obesity results from a chronic imbalance between energy intake and energy expenditure, resulting in increased fat storage. The mechanism of obesity is not fully understood however, the complex interactions of neural, hormonal, genetic and environmental factors due to Westernized diet are thought to induce this obesity epidemic. Over accumulation of fat might be a high risk factor for various metabolic syndromes such as diabetes, hypertension, dyslipidaemia and cardiovascular disease. (Manson et al., *New England J. Med.*, 333, pp 677-685, 1995; Kopleman P. G., *Nature*, 404 pp 635-643, 2000; Must et al., *JAMA* 282, pp 1523-1529. 1999).

Although there are several well-known representative anti-obesity agents such as Xenical™ (Roche Pharm. Co Ltd. Swiss), Reductil™ (Abbot Co Ltd. USA) and Exolise™ (Atopharma Co Ltd. France), more effective agents have been needed because of their side effects such as heart disease, respiratory disease and neuronal system disorder.

Recent strategies for developing anti-obesity agent are focused on reducing diet, inhibiting calorie intake, stimulating thermogenic reaction, regulating energy metabolism, and controlling signal transduction through neuronal nerve system (Kopleman P. G., *Nature*, 404 pp 635-643, 2000). There have been many attempts to develop effective anti-obesity agents, however satisfactory drugs showing potent efficacy as well as safety have not been developed yet.

Accordingly, the attempts to develop an effective anti-obesity agent with natural products of which safety has been verified are more effective rather than them with synthetic substance.

Most of the plants belonged to Cucurbitaceae family of Dicotyledonaceae class are annual or perrenial viny plants and distributed in tropical and subtropical zone. Among them, *Melothris japonica*, *Schzopepon bryoniaefolius*, *Gynostemma pentaphyllum* and the like have been distributed, and pumpkin (*Cucurbita moschata* DUCH), water melon (*Citrullus vulgaris* SCHRAD), sponge gourd (*Luffa cylindrical* L. ROEM), cucumber (*Cucumis sativus* L) and the like have been cultivated in Korea.

It has been reported that pumpkin (*Cucurbita moschata* DUCH) comprising cucurbitine and fat oils such as linoleic acid, oleic acid, carotene etc shows anthelmintic activity; water melon (*Citrullus vulgaris* SCHRAD) comprising citrulline, alanine, fructose, glucose etc shows potent diuretic activity; sponge gourd (*Luffa cylindrical* L. ROEM) is used as a washing tool; and cucumber (*Cucumis sativus* L) comprising glycoside, caffeic acid, cucurbitacins etc shows diuretic activity according to the literature (Chung B. S et al: HyangyakDaesajeon, young-rim press, pp 945-957, 1998).

However, there has been not reported or disclosed on the preventing or treating activity of the alcohol compound isolated from the extract of Cucurbitaceae family plant showing potent anti-obesity effects in any of above cited literatures, and the disclosures of which are incorporated herein by reference.

To investigate the anti-obesity effect of the alcohol compound isolated from the extract of Cucurbitaceae family plant, the inventors of present invention have intensively carried out various in vitro experiments testing the inhibitory effects on adipocyte differentiation and triglyceride synthesis. And also the inventors investigated the activity of this extracts to activate transcription factor, PPAR α regulating the expression of genes involved in adipocytes differentiation. This extracts showed no toxicity in animal test and reduced the body weight of test animals. As a result of these investigations, the inventors finally completed the present invention by confirming that the alcohol compound isolated from the extract of Cucurbitaceae family strongly inhibited the adipocyte differentiation and reduced the body weight of animals. These results suggested that this compound had the potential to be an effective anti-obesity agent.

DISCLOSURE

Accordingly, the present invention provides a pharmaceutical composition comprising dehydrodiconiferyl alcohol of following chemical formula (1a) isolated from the extract of Cucurbitaceae family plant and the pharmacologically acceptable salt thereof having anti-adipogenic and anti-obesity effect as an active ingredient in an effective amount to treat and prevent obesity and adipogenesis-involved diseases.

(1a)

The term "the Cucurbitaceae family plant" disclosed herein comprises pumpkin (*Cucurbita moschata* DUCH), water melon (*Citrullus vulgaris* SCHRAD), sponge gourd (*Luffa cylindrical* L. ROEM), gourd (*Lagenaria siceraria* STANDL. var. *depressa* HERA), and cucumber (*Cucumis sativus* L), preferably, pumpkin (*Cucurbita moschata* DUCH), water melon (*Citrullus vulgaris* SCHRAD), and sponge gourd (*Luffa cylindrical* L. ROEM).

Above-described "extract" comprises crude extract or non-polar solvent soluble extract of the herb, fruit, stem and leaf, preferably, the stem or leaf of Cucurbitaceae family Cucurbitaceae family plant.

It is an object of the present invention to provide the dehydrodiconiferyl alcohol isolated from Cucurbitaceae family plant as a material of health care food or food additives or a pharmacologically acceptable salt to prepare therapeutic agent for the treatment and prevention of obesity and adipogenesis-involved diseases of mammal including human.

The term "obesity and adipogenesis-involved diseases" contains obesity, type II diabetes, steatosis, hyperlipemia, cardiovascular disease, artherosclerosis and the like.

The pharmaceutical composition of the present invention can contain about 0.02~90% by weight of the above compound based on the total weight of the composition.

The health care food of the present invention comprises the above compound as 0.01 to 80%, preferably 1 to 50% by weight based on the total weight of the composition.

Above health care food can be contained in health care food, health beverage etc, and may be used as powder, granule, tablet, chewing tablet, capsule, beverage etc.

An inventive compound isolated from the extract of Cucurbitaceae family plant may be prepared in accordance with the following preferred embodiment.

Hereinafter, the present invention is described in detail.

An inventive compound isolated from the extract of Cucurbitaceae family plant can be prepared in detail by following procedures, The inventive compound isolated from the extract of Cucurbitaceae family plant can be prepared by follows; the stem or leaf of Cucurbitaceae family plant such as pumpkin, water melon or sponge gourd is dried, cut, crushed and mixed with 1 to 25-fold, preferably, approximately 5 to 15 fold volume of distilled water, lower alcohols such as methanol, ethanol, butanol and the like, or the mixtures thereof, preferably methanol; the solution is treated with hot water at the temperature ranging from 20 to 100° C., preferably from 70 to 100° C., for the period ranging from 30 min to 24 hours, preferably, 30 min to 3 hours with extraction method such as extracting with hot water, cold water, reflux extraction, or ultra-sonication extraction with 1 to 5 times, preferably 2 to 3 times, consecutively; the residue is filtered to obtain the supernatant to be concentrated with rotary evaporator, at the temperature ranging from 20 to 100° C., preferably from 50 to 70° C. and then dried by vacuum freeze-drying, hot air-drying or spray drying to obtain dried crude extract powder of crude extract of Cucurbitaceae family plant which can be soluble in water, lower alcohols, or the mixtures thereof.

Additionally, polar-solvent soluble and non-polar solvent soluble extract of present invention can be prepared by following procedure; the crude extract prepared by above described step, is suspended in water, and then is mixed with 1 to 100-fold, preferably, 1 to 5-fold volume of non polar solvent such as ethyl acetate, chloroform, hexane and the like; the non-polar solvent soluble layer is collected to obtain non-polar solvent soluble extract of the present invention and remaining polar solvent soluble layer is collected to obtain polar solvent soluble extract of the present invention which is soluble in water, lower alcohols, or the mixtures thereof. Also, above described procedures may be modified or subjected to further step to fractionate or isolate more potent fractions or compounds by conventional procedure well-known in the art, for example, the procedure disclosed in the literature (Harborne J. B. Phytochemical methods: A guide to modern techniques of plant analysis, $3^{rd}$ Ed. pp 6-7, 1998).

Additionally, inventive compound which could be prepared by subjecting chloroform soluble fraction showing most potent anti-adipogenic and anti-obesity activity to silica gel column chromatography with a solvent mixture mixed with hexane:chloroform:methanol (16:15:1) to afford 11 sub-fractions; subjecting $9^{th}$ faction among said sub-fractions showing most potent anti-adipogenenic and anti-obesity activity to repetitive silica gel column chromatography with a solvent mixture mixed with chloroform:methanol (30:1) and HPLC using methanol ranging from 20 to 70% as a mobile phase and running 40% methanol with a flow velocity of 2 ml/m to obtain inventive dehydrodiconiferyl alcohol.

Alternatively, The inventive compound of the present invention for may be also synthesized by the conventional synthetic method in accordance with a using method well known in the art (Herbert O. House, *Modern Synthetic Reactions*, $2^{nd}$ Ed., The Benjamin/Cummings Publishing Co., 1972).

The inventive compounds represented by chemical formula (1a) can be transformed into their pharmaceutically acceptable salt and solvates by the conventional method well known in the art. For the salts, acid-addition salt thereof formed by a pharmaceutically acceptable free acid thereof is useful and can be prepared by the conventional method. For example, after dissolving the compound in the excess amount of acid solution, the salts are precipitated by the water-miscible organic solvent such as methanol, ethanol, acetone or acetonitrile to prepare acid addition salt thereof and further the mixture of equivalent amount of compound and diluted acid with water or alcohol such as glycol monomethylether, can be heated and subsequently dried by evaporation or filtrated under reduced pressure to obtain dried salt form thereof.

As a free acid of above-described method, organic acid or inorganic acid can be used. For example, organic acid such as methansulfonic acid, p-toluensulfonic acid, acetic acid, trifluoroacetic acid, citric acid, maleic acid, succinic acid, oxalic acid, benzoic acid, lactic acid, glycolic acid, gluconic acid, galacturonic acid, glutamic acid, glutaric acid, glucuronic acid, aspartic acid, ascorbic acid, carbonylic acid, vanillic acid, hydroiodic acid and the like, and inorganic acid such as hydrochloric acid, phosphoric acid, sulfuric acid, nitric acid, tartaric acid and the like can be used herein.

Further, the pharmaceutically acceptable metal salt form of inventive compound may be prepared by using base. The alkali metal or alkali-earth metal salt thereof can be prepared by the conventional method, for example, after dissolving the compound in the excess amount of alkali metal hydroxide or alkali-earth metal hydroxide solution, the insoluble salts are filtered and remaining filtrate is subjected to evaporation and drying to obtain the metal salt thereof. As a metal salt of the present invention, sodium, potassium or calcium salt are pharmaceutically suitable and the corresponding silver salt can be prepared by reacting alkali metal salt or alkali-earth metal salt with suitable silver salt such as silver nitrate.

The pharmaceutically acceptable salt of the compound represented by chemical formula (1a) comprise all the acidic or basic salt which may be present at the compounds, if it does not indicated specifically herein. For example, the pharmaceutically acceptable salt of the present invention comprise the salt of hydroxyl group such as the sodium, calcium and potassium salt thereof; the salt of amino group such as the hydrogen bromide salt, sulfuric acid salt, hydrogen sulfuric acid salt, phosphate salt, hydrogen phosphate salt, dihydrophosphate salt, acetate salt, succinate salt, citrate salt, tartarate salt, lactate salt, mandelate salt, methanesulfonate(mesylate) salt and p-toluenesulfonate (tosylate) salt etc, which can be prepared by the conventional method well known in the art.

It is confirmed that the compound of the present invention strongly inhibited the accumulation of adipocyte and triglycerides, and reduced the body weight therefore it can be useful as a potent anti-obesity agent.

The compound according to the present invention can be provided as a pharmaceutical composition containing pharmaceutically acceptable carriers, adjuvants or diluents. For example, the compound of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

The compound of the present invention has potent anti-obesity and anti-adipogenecity activity, and the pharmaceutical composition of the present invention thus may be employed to treat or prevent obesity and adipogenesis-involved diseases.

Hereinafter, the following formulation methods and excipients are merely exemplary and in no way limit the invention.

The compound of the present invention in pharmaceutical dosage forms may be used in the form of their pharmaceutically acceptable salts, and also may be used alone or in appropriate association, as well as in combination with other pharmaceutically active compounds.

The compound of the present invention may be formulated into preparations for injections by dissolving, suspending, or emulsifying them in aqueous solvents such as normal saline, 5% Dextrose, or non-aqueous solvent such as vegetable oil, synthetic aliphatic acid glycerides, esters of higher aliphatic acids or propylene glycol. The formulation may include conventional additives such as solubilizers, isotonic agents, suspending agents, emulsifying agents, stabilizers and preservatives.

The desirable dose of the inventive compound varies depending on the condition and the weight of the subject, severity, drug form, route and period of administration, and may be chosen by those skilled in the art. However, in order to obtain desirable effects, it is generally recommended to administer at the amount ranging 0.0001-100 mg/kg, preferably 0.001-100 mg/kg by weight/day of the inventive compound of the present invention. The dose may be administered in single or divided into several times per day. In terms of composition, the compounds should be present between 0.0001 to 10% by weight, preferably 0.0001 to 1% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intrathecal, epidural or intracerebroventricular injection.

The compound of the present invention also can be used as a main component or additive and aiding agent in the preparation of various functional health food and health care food.

The term "a functional health food" defined herein means "the functional food having enhanced functionality such as physical functionality or physiological functionality by adding the compound of the present invention to conventional food to prevent or improve obesity and adipogenesis-involved diseases in human or mammal.

It is the other object of the present invention to provide a health care food comprising a dehydrodiconiferyl alcohol isolated from Cucurbitaceae family plant and the pharmacologically acceptable salt thereof, together with a sitologically acceptable additive for the prevention and alleviation of obesity and adipogenesis-involved diseases.

The term "a health care food" defined herein means "the food containing the compound of the present invention showing no specific intended effect but general intended effect in a small amount of quantity as a form of additive or in a whole amount of quantity as a form of capsule, pill, tablet etc.

The term "a sitologically acceptable additive" defined herein "any substance the intended use which results or may reasonably be expected to result-directly or indirectly-in its becoming a component or otherwise affecting the characteristics of any food" for example, thickening agent, maturing agent, bleaching agent, sequesterants, humectant, anticaking agent, clarifying agents, curing agent, emulsifier, stabilizer, thickner, bases and acid, foaming agents, nutrients, coloring agent, flavoring agent, sweetner, preservative agent, antioxidant, etc, which shall be explained in detail as follows.

If a substance is added to a food for a specific purpose in that food, it is referred to as a direct additive and indirect food additives are those that become part of the food in trace amounts due to its packaging, storage or other handling.

Above described health foods can be contained in food, health beverage, dietary therapy etc, and may be used as a form of powder, granule, tablet, chewing tablet, capsule, beverage etc for preventing or improving obesity and adipogenesis-involved diseases.

Also, above described compound can be added to food or beverage for prevention and improvement of obesity and adipogenesis-involved diseases. The amount of above described compound in food or beverage as a functional health food or health care food may generally range from about 0.01 to 100 w/w % of total weight of food for functional health food composition. In particular, although the preferable amount of the compound of the present invention in the functional health food or health care food may be varied in accordance to the intended purpose of each food, it is preferably used in general to use as a additive in the amount of the compound of the present invention ranging from about 0.01 to 5% in food such as noodles and the like, from 40 to 100% in health care food on the ratio of 100% of the food composition.

Providing that the health beverage composition of present invention contains above described compound as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese, chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition. Examples of addable food comprising aforementioned extract therein are various food, beverage, gum, vitamin complex, health improving food and the like.

The present invention is more specifically explained by the following examples. However, it should be understood that the present invention is not limited to these examples in any manner.

DESCRIPTION OF DRAWINGS

FIGS. 1 and 2 show the inhibition effect of the present compound on the adipocytes differentiation and triglyceride level.

BEST MODE

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Reference Example, Examples and Experimental Examples are intended to further illustrate the present invention without limiting its scope.

Example 1

Preparation of Dehydrodiconiferyl Alcohol Isolated from the Extract of Cucurbitaceae Plant 1.1 Preparation of Crude Extract Each 2 kg of dried stems and leaves of pumpkin (*Cucurbita moschata* DUCH), water melon (*Citrullus vulgaris* SCHRAD), and sponge gourd (*Luffa cylindrical* L. ROEM) purchased from Korean market was cut, mixed with 20 l of methanol and extracted for 1 hour at 90° C. with reflux extraction apparatus. Above extraction steps were repeated three times to collect supernatant, and this crude extracts were filtrated with filter paper and the filtrate was concentrated under reduced pressure to obtain each dried hot-water extracts of pumpkin, water melon, and sponge gourd respectively as shown in Table 1.

TABLE 1

| Material | The amount of final crude extract (g) |
|---|---|
| The stem of pumpkin | 300 |
| The leaves of pumpkin | 400 |
| The stem of water-melon | 350 |
| The leaves of water-melon | 360 |
| The stem of sponge gourd | 240 |
| The leaves of sponge gourd | 290 |

1.2 Preparation of Chloroform Soluble Extract 200 g of dried hot-water soluble extract of pumpkin prepared in Example 1-1 was suspended with 1 L of distilled water and 1 L of hexane was added thereto. The solution was subjected to fractionation with hexane layer and water layer three times and then the collected hexane layer was filtrated and dried with rotary vacuum evaporator to obtain 180 mg of hexane soluble extract. 1 l of chloroform was added to remaining water extract and subjected to repeated fractionation to obtain 770 mg of chloroform soluble extract. 1 l of ethylacetate was added to remaining water extract and subjected to repeated fractionation to obtain 2.1 g of ethylacetate soluble extract. 1 l of butanol was added to remaining water extract and subjected to repeated fractionation to obtain 7.4 g of butanol soluble extract and water soluble extract.

1.3 Preparation of Dehydrodiconiferyl Alcohol 770 mg of chloroform soluble extract was subjected to Silica gel column chromatography using column (3×27 cm) filled with 25 g of silica gel (Merck Co. No-9385) and eluting with solvent mixture (hexane:chloroform:methanol=16:15:1) as a mobile phase. Collected fractions were dried to afford 11 fractions, i.e., 1st fraction (31 mg), 2nd fraction (18 mg), 3rd fraction (65 mg), 4th fraction (18 mg), 5th fraction (54 mg), 6th fraction (75 mg), 7th fraction (39 mg), 8th fraction (200 mg), 9th fraction (20 mg), 10th fraction (163 mg) and 11th fraction (64 mg). 20 mg of 9th fraction showing most potent anti-obesity activity was subjected to silica gel column chromatography filled with 2 g of silica gel (Merck 9385) and eluted with a stepwise application of solvent mixture containing linear gradient of chloroform:methanol (30:1?>10:1). To purify the 9th fraction further, HPLC (u-Bondapak C18, Waters, 7.8×300 mm column, detector: UV 254 nm) using methanol ranging from 20 to 70% as a mobile phase and running 40% methanol with a flow velocity of 2 ml/m was performed to obtain dehydrodiconiferyl alcohol having following physicochemical property, of which data were consistent to those data disclosed in the literature (Kuroda et al., *J. Agric. Food. Chem.*, 50, pp 3396-3400, 2002).

Dehydrodiconiferyl Alcohol: $C_{22}H_{22}O_6$ (M.W: 338)

$^1$H-NMR (400 MHz, acetone-$d_6$); δ 3.53 (1H, d, J=6.8 Hz, b-H), 3.82 (3H, s, O $CH_3$), 3.81 (1H, dd, J=11.2, 6.8 Hz, g-H), 3.90 (1H, dd, J=11.2, 5.2 Hz, g-H), 4.20 (2H, dd, J=5.2, 1.6 Hz, g'-H2), 5.56 (1H, d, J=6.8 Hz, a-H), 6.24 (1H, dt, J=16.0, 1.6 Hz, a'-H), 6.81 (1H, d, J=8.0 Hz, 5-H), 6.88 (1H, dd, J=8.0, 2.2 Hz, 6-H), 6.95 (1H, J=1.6 Hz, 2'-H), 6.98 (1H, d, J=1.6, 6'-H), 7.04(1H, d, J=2.0 Hz, 2-H);

$^{12}$C-NMR (100 MHz, acetone-$d_6$); δ 54.74 (C-b), 56.21 ($OCH_3$), 56.32 ($OCH_3$), 63.35 (C-g'), 64.56 (C-g), 88.49 (C-a), 110.43 (C-2), 11.62 (C-2'), 115.62 (C-5), 116.04 (C-6'), 119.54 (C-6), 128.34 (C-b'), 130.37 (C-a'), 130.47 (C-5'), 131.89 (C-1'), 134.35 (C-1), 145.22 (C-3'), 147.41 (C-4), 148.43 (C-3), 149.02 (C-4').

Experimental Example 1

Inhibition Effect on the Adipocytes Differentiation and Triglyceride Level

To determine the inhibiting activity of the compound prepared by Examples 1, i.e., dehydrodiconiferylalcohol (DHCA), on the adipocytes differentiation and triglyceride level, following experiment was performed.

Preadipocytes (3T3-L1) purchased from ATCC (American Tissue Culture Collection, USA) were cultured in RPMI medium containing 10% FBS and MDI cocktail (isobutylmethylxanthine, dexamethasone, insulin) was added thereto for differentiating into mature adipocytes. After two days, the medium was replaced and treated with only insulin. Thereafter, the medium was replaced and equal concentration of insulin was treated again every other day. DHCA ranging from 10 to 1000 ug/ml of the concentrations was treated when the adipocyte differentiation was induced and equal concentration of the DHCA was treated at every replacement of the medium. Troglitazone (Sigma Co.) and 10 uM SB203580 (Sigma Co.) were treated as control groups and 0.01% ethanol was used as a vehicle control. After eight days lapsed, the accumulated fat within differentiated cell was stained with Oil Red 0 staining reagent and the absorbance was determined with optical density qualitatively at 490 nm. The inhibition percentage (%) was calculated by following Empirical Formula 1.

The Inhibition Percentage (%)=[*O.D.* of test group]/
[*O.D.* value of control group]×100       Empirical Formula 1

Figure 1:
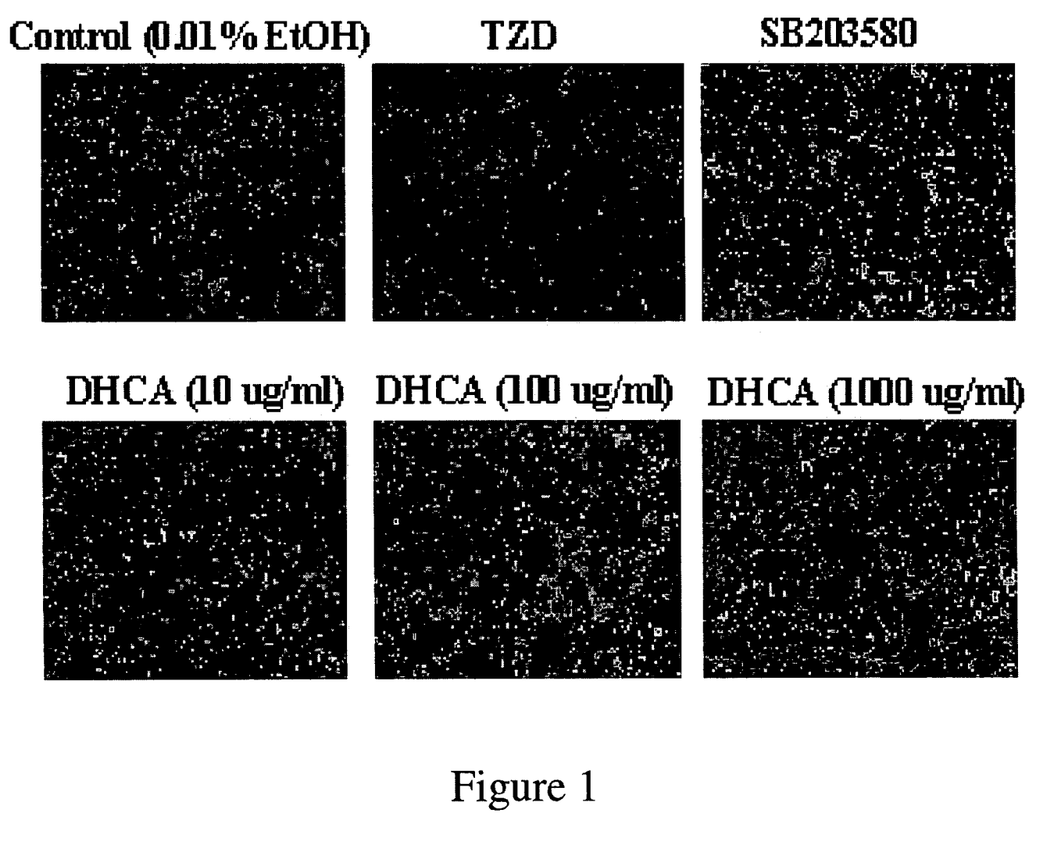
FIG. 1 shows a photomicrograph showing the inhibition effect and FIG. 2 shows a graph showing the inhibition effect.
Figure 2:
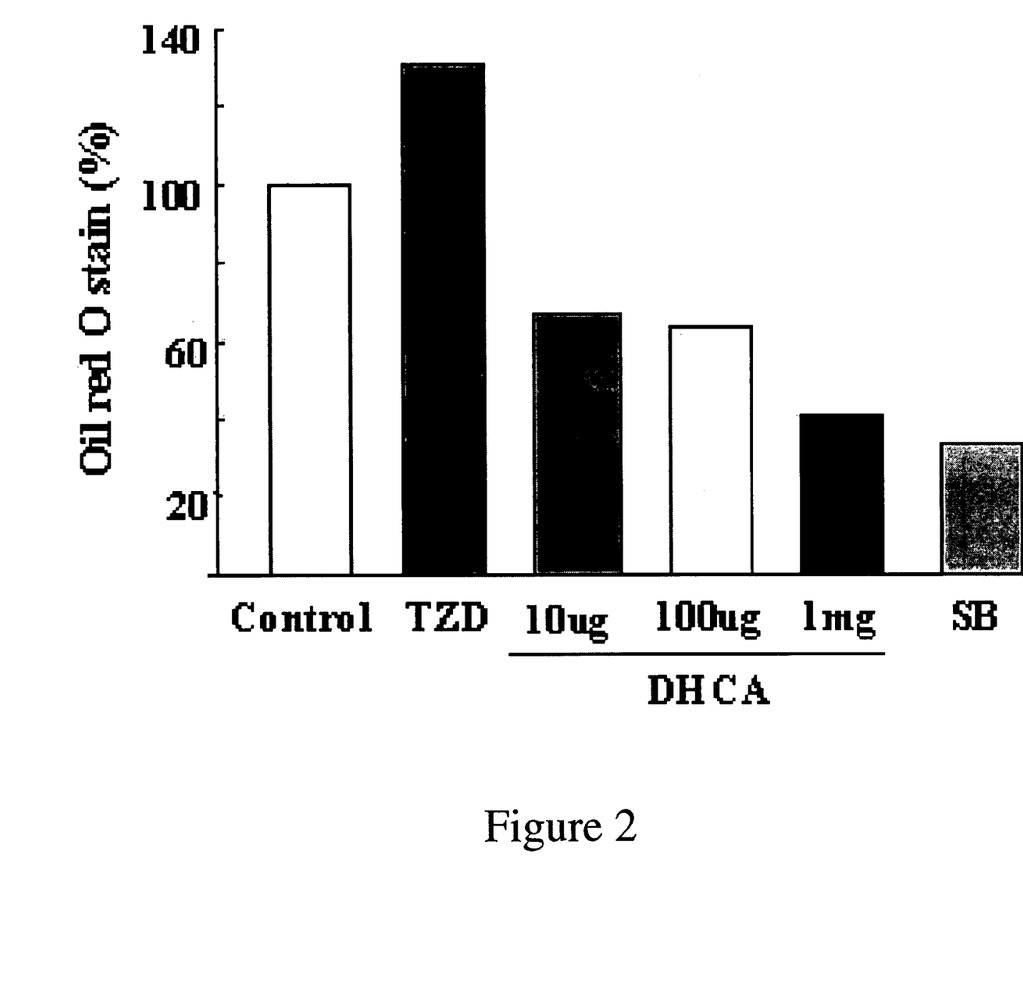

As the result, it is confirmed that preadipocytes, 3T3-L1 cells were differentiated into mature ones and triglyceride was accumulated in large doplets within fully differentiated cells. In the adipocyte differentiation stimulator troglitazone treatment group, the triglyceride was more produced and the red color was more intensified than those of other groups. The level of produced triglycerides and the adipocytes differentiation in the test sample treatment group was significantly reduced in a dose dependent manner. This anti-adipogenic activity of DHCA was comparable to that of SB203580 known to inhibit adipocyte differentiation (FIG. 1 to FIG. 2)

Experimental Example 2

Regulation Effect on the PPAR α Activation

To determine the regulating activity of the compound prepared by Example 1 on the PPAR α activation, following experiment was performed.

CV-1 cells were transiently cotransfected with both tkP-PRE-luciferase and pCMV-PPAR α, together with pCMV-RXR and pCMV-β-Gal as a transfection control. Cells were treated with DHCA or various fractions, i.e. hexane and ethylacetate fractions obtained from this Cucurbitaceae family plant extract at the concentration of 100 ug/ml. Cells were also treated with DMSO or fenofibrate (100 uM, Sigma Co.), which is a well known agonist of PPARα. After 24 hours, cell lysates were prepared for the luciferase assay, and the activities were normalized to β-Gal activities.

Figure 3:
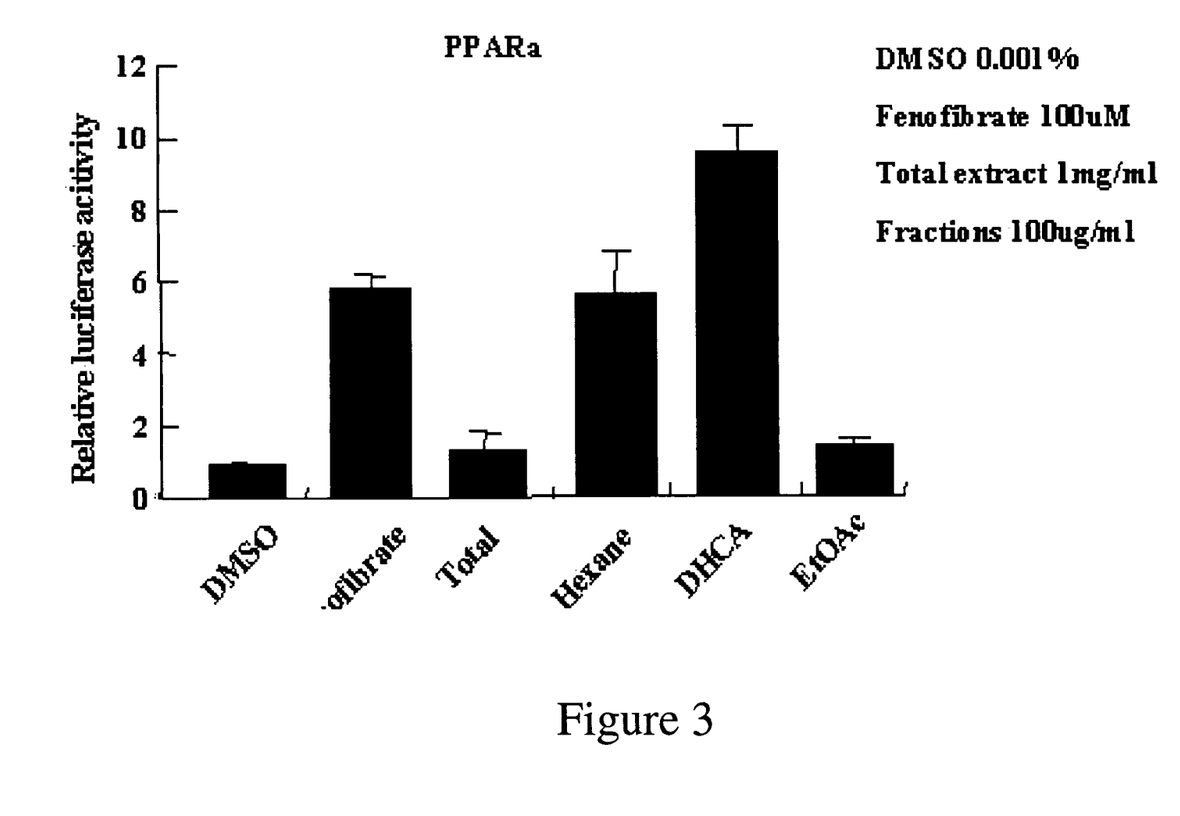
FIG. 3 shows the regulation effect of the present compound on the activity of PRARs.

As clearly shown in FIG. 3, DHCA, but not Cucurbitaceae family plant total extract itself, increased the level of luciferase activity by 10 folds as compared with that of the control. The magnitude of activation in cells treated with the DHCA was higher than that of fenofibrate treated cells, suggesting that the DHCA (dehydrodiconiferyl alcohol) isolated from the extract of Cucurbitaceae family plant can regulate lipid metabolism through PPAR α activation.

Experimental Example 3

Toxicity Test

Methods

The acute toxicity tests for the test compounds on six weeks aged SPF SD rats were performed by following procedure.

Four groups consisting of 2 rats was administrated orally with 100 mg/kg of the crude extract and observed for 2 weeks.

Results

There were no treatment-related effects on mortality, clinical signs, body weight changes and gross findings in any group or either gender. The minimum $LD_{50}$ value in oral administration was more than 100 g/kg. These results suggested that the test compounds prepared in the present invention were potent with safe.

Hereinafter, the formulating methods and kinds of excipients will be described, but the present invention is not limited to them. The representative preparation examples were described as follows.

Preparation of Powder

| | |
|---|---|
| DHCA | 50 mg |
| Lactose | 100 mg |
| Talc | 10 mg |

Powder preparation was prepared by mixing above components and filling sealed package.

Preparation of Tablet

| | |
|---|---|
| DHCA | 50 mg |
| Corn Starch | 100 mg |
| Lactose | 100 mg |
| Magnesium Stearate | 2 mg |

Tablet preparation was prepared by mixing above components and entabletting.

Preparation of Capsule

| | |
|---|---|
| DHCA | 50 mg |
| Corn starch | 100 mg |
| Lactose | 100 mg |
| Magnesium Stearate | 2 mg |

Tablet preparation was prepared by mixing above components and filling gelatin capsule by conventional gelatin preparation method.

Preparation of Injection

| | |
|---|---|
| DHCA | 50 mg |
| Distilled water for injection | optimum amount |
| pH controller | optimum amount |

Injection preparation was prepared by dissolving active component, controlling pH to about 7.5 and then filling all the components in 2 ml ample and sterilizing by conventional injection preparation method.

Preparation of Liquid

| | |
|---|---|
| DHCA | 0.1~80 g |
| Sugar | 5~10 g |
| Citric acid | 0.05~0.3% |
| Caramel | 0.005~0.02% |
| Vitamin C | 0.1~1% |
| Distilled water | 79~94% |
| $CO_2$ gas | 0.5~0.82% |

Liquid preparation was prepared by dissolving active component, filling all the components and sterilizing by conventional liquid preparation method.

Preparation of Health Care Food

| | |
|---|---|
| DHCA | 1000 mg |
| Vitamin mixture | optimum amount |
| Vitamin A acetate | 70 mg |
| Vitamin E | 1.0 mg |
| Vitamin $B_1$ | 0.13 mg |
| Vitamin $B_2$ | 0.15 mg |
| Vitamin B6 | 0.5 mg |
| Vitamin B12 | 0.2 mg |
| Vitamin C | 10 mg |
| Biotin | 10 mg |
| Amide nicotinic acid | 1.7 mg |
| Folic acid | 50 μg |
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The above-mentioned vitamin and mineral mixture may be varied in many ways. Such variations are not to be regarded as a departure from the spirit and scope of the present invention.

Preparation of Health Beverage

| | |
|---|---|
| DHCA | 1000 mg |
| Citric acid | 1000 mg |
| Oligosaccharide | 100 g |
| Apricot concentration | 2 g |
| Taurine | 1 g |
| Distilled water | 900 ml |

Health beverage preparation was prepared by dissolving active component, mixing, stirred at 85° C. for 1 hour, filtered and then filling all the components in 1000 ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the compound isolated from the extract of Cucurbitaceae family plant of the present invention showed potent reducing activity of body weight, decreasing effect on the blood triglyceride and cholesterol level, activating activity of PPAR α, and preventing activity from the adipogenesis of precursor fat cells with no toxicity, therefore, the compound can be useful in treating or preventing obesity and adipogenesis-involved diseases as a medicine or health care food.

What is claimed is:

1. A method of treatment to induce an anti-obesity effect comprising the step of administering an effective amount of dehyrodiconiferyl alcohol (DHCA) of formula (1a) into a subject in need thereof, (1a)

wherein the anti-obesity effect is selected from the group consisting of (i) inhibiting adipocyte differentiation, (ii) inhibiting triglyceride synthesis, (iii) activating PPAR alpha and (iv) reducing body weight.

2. The method of claim 1, wherein the DHCA is extracted from a Cucurbitaceae family plant selected from the group consisting of pumpkin (*Cucurbita moschata* DUCH), watermelon (*Citrullus vulgaris* SCHRAD), sponge gourd (*Luffa cylindrical* L. ROEM), gourd (*Lagenaria siceraria* STANDL. var, depressa HERA), and cucumber (*Cucumis sativus* L).

3. The method of claim 2, wherein the DHCA is extracted from the stem or leaf of the Cucurbitaceae family plant.

4. The method of claim 1, wherein the subject is a human.

5. The method of claim 1, wherein DHCA is administered to the subject in an amount ranging from 0.0001 to 100 mg/kg by weight/day.

* * * * *